United States Patent [19]
Hughes

[11] Patent Number: 6,024,891
[45] Date of Patent: *Feb. 15, 2000

[54] SILICONE COMPOSITIONS

[75] Inventor: Iain Allan Hughes, Surrey, United Kingdom

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/860,061

[22] PCT Filed: Dec. 5, 1995

[86] PCT No.: PCT/US95/15765

§ 371 Date: Jun. 23, 1997

§ 102(e) Date: Jun. 23, 1997

[87] PCT Pub. No.: WO96/19562

PCT Pub. Date: Jun. 27, 1996

[30] Foreign Application Priority Data

Dec. 22, 1994 [GB] United Kingdom .................... 9425943

[51] Int. Cl.[7] .......................... C01B 15/055; C01B 15/06; C01B 15/16; A61K 7/20
[52] U.S. Cl. .................................. 252/186.31; 252/186.3; 252/186.27; 252/186.38; 510/309; 510/312; 424/53; 424/54
[58] Field of Search ............................. 252/186.27, 186.3, 252/186.31, 186.44, 186.38; 510/309, 312, 313, 117, 275; 424/49, 53, 54

[56] References Cited

U.S. PATENT DOCUMENTS

| | | | |
|---|---|---|---|
| 4,619,779 | 10/1986 | Hardy | 252/186.26 |
| 5,041,280 | 8/1991 | Smigel | 424/52 |
| 5,045,225 | 9/1991 | Aronson et al. | |
| 5,106,609 | 4/1992 | Bolich, Jr. et al. | 424/70 |
| 5,143,518 | 9/1992 | Madrange et al. | 8/405 |
| 5,154,915 | 10/1992 | Weber et al. | 424/54 |
| 5,186,926 | 2/1993 | Williams et al. | 424/53 |
| 5,188,822 | 2/1993 | Viccaro et al. | 424/52 |
| 5,192,532 | 3/1993 | Guay et al. | 424/53 |
| 5,424,060 | 6/1995 | Hauschild | 424/52 |

*Primary Examiner*—Joseph D. Anthony
*Attorney, Agent, or Firm*—Betty J. Zea; T. David Reed

[57] ABSTRACT

This invention relates to a method of improving the stability of a bleach and lipophile composition comprising an inorganic persalt bleaching agent and a lipophile selected from the group consisting of flavorants, perfumes, coolants, antimicrobial agents, and mixtures thereof, by inclusion of an aminoalkylsilicone, having an aminoalkylsiloxane content of from about 0.1% to 2% on a repeating unit basis.

13 Claims, No Drawings

SILICONE COMPOSITIONS

This application is a 371 of PCT/US95/15765, filed Dec. 5, 1995.

TECHNICAL FIELD

The present invention relates to silicone-containing compositions and to use thereof in various household products such as personal care products, laundry and household cleaners, bleaching compositions and the like. In particular, it relates to silicone-containing lipophilic compositions based on flavorants, perfumes, coolants or antimicrobial agents as lipophile and which display improved residuality, impact and/or efficacy on surfaces treated therewith, for example teeth, dentures, skin, hair, laundry, dishware, working surfaces and the like. In addition, it relates to silicone-containing bleach compositions which additionally contain bleach-sensitive ingredients such as perfumes, flavorants and the like and which display improved stability.

BACKGROUND

Lipophilic compositions such as flavor, perfume, coolant and disinfectant compositions are widely used either directly or in a variety of household products inclusive of cosmetics, oral and denture compositions, bleach, dishwashing, hard surface cleaning and laundry detergent products, etc. A common problem encountered with lipophilic compositions is that of improving surface substantivity or residuality of the lipophilic component. It would be desirable in many if not most household applications to enhance the surface residuality of the lipophile in order, for example, to provide increased flavor or perfume impact or increased antimicrobial efficacy.

Modern dental hygiene and denture preparations, for example, typically contain antiplaque and/or antitartar agents, as well as antimicrobial agents and flavorants. Antimicrobial action could affect plaque formation by either reducing the number of bacteria in the mouth/dentures or by killing those bacteria trapped in the film to prevent further growth and metabolism. Flavorants may alleviate the problem of bad breath via a deodorizing action. Some antimicrobial agents, e.g. menthol may, also serve as breath deodorizers. However, the efficacy of antimicrobial agents depends largely on their intraoral/denture retention, particularly their retention on the surface of the teeth or dentures where plaque is formed.

A typical disadvantage of known dental preparations is that only a relatively short time during which the teeth are being cleaned or the mouth is being rinsed is available for antimicrobial agents in the preparations to take effect. The problem is compounded by the fact that dentifrice preparations are used infrequently; most are used once or, perhaps, twice daily. Consequently, the long time period between brushings for a majority of the population provides optimum plaque forming conditions.

In many other personal and household applications, it would be desirable to provide enhanced surface substantivity. Laundry detergents, for example, would benefit by increasing perfume substantivity on fabrics so as to provide increased perfume impact on clothing after laundering or during use. Increased antimicrobial substantivity would also be beneficial from the viewpoint of reducing malodors associated with sweat or other soils. Enhanced perfume substantivity would also be valuable in fine fragrance and perfumed cosmetics. Enhanced coolant substantivity, on the other hand, would be beneficial in cough/cold products.

There has been a need, therefore, for developing lipophilic compositions which have improved surface residuality, impact and/or antimicrobial efficacy.

The use of lipophilic compounds such as perfumes, flavorants and the like in bleach-containing compositions can also raise a number of problems, especially loss of perfume or flavorant character or intensity as a result of interaction with the bleach. The efficacy of the bleaching agent can also be adversely effected. It would thus be desirable to improve the stability and effectiveness of bleach compositions containing bleach-sensitive ingredients.

It is known to include silicones in dentifrice compositions, allegedly to coat the teeth and prevent cavities and staining. For instance, GB-A-689,679 discloses a mouthwash containing an organopolysiloxane for preventing adhesion of, or for removing tars, stains, tartar and food particles from the teeth. The mouthwash may include antiseptic compounds, such as thymol, and flavoring and perfuming agents.

U.S. Pat. No. 2,806,814 discloses dental preparations including, in combination, a higher aliphatic acyl amide of an amino carboxylic acid compound as an active and a silicone compound. The patent notes that silicone compounds have been proposed for prevention of adhesion or to facilitate the removal of tars, stains, tartar and the like from teeth. The silicone compound is said to act as a synergist in improving the antibacterial and acid inhibiting activity of the active ingredient. Dimethyl polysiloxanes are said to be particularly effective. Flavoring oils and/or menthol may be included.

U.S. Pat. No. 3,624,120 discloses quaternary ammonium salts of cyclic siloxane polymers for use as cationic surfactants, bactericides and as anticariogenic agents.

Accordingly, the present invention provides a flavor, perfume, coolant, antimicrobial or other lipophilic composition having improved surface-substantivity, impact and/or efficacy.

The invention further provides a bleach composition comprising an inorganic persalt bleaching agent, and a lipophilic compound such as a flavorant and/or perfume and which has improved stability.

SUMMARY OF THE INVENTION

According to a first aspect of the invention, there is provided a flavor, perfume, coolant, antimicrobial or other lipophilic composition comprising an aminoalkylsilicone having an aminoalkylsiloxane content of from about 0.1%–2% on a repeating unit basis.

The invention also relates to the use of an aminoalkylsilicone with a lipophile selected from flavorants, perfumes, physiological coolants, antimicrobial agents and mixtures thereof to provide improved surface residuality, wherein the aminoalkylsilicone is selected from aminoalkylsilicones having an aminoalkylsiloxane content of from about 0.1%–2% on a repeating unit basis.

According to a further aspect of the invention, there is provided a bleach composition comprising an inorganic persalt bleaching agent, a lipophile selected from flavorants, perfumes, physiological coolants, antimicrobial agents and mixtures thereof, and an aminoalkylsilicone having an aminoalkylsiloxane content of from about 0.1%–2% on a repeating unit basis.

The invention also relates to the use of an aminoalkylsilicone with an inorganic persalt bleaching agent and a lipophile selected from flavorants, perfumes, physiological coolants, antimicrobial agents and mixtures thereof to provide improved lipophile stability, wherein the aminoalkylsilicone is selected from aminoalkylsilicones having an aminoalkylsiloxane content of from about 0.1%–2% on a repeating unit basis.

All percentages and ratios herein are by weight of total composition, unless otherwise indicated.

The compositions of the invention thus comprise an aminoalkylsilicone antiplaque agent and a lipophile selected from flavorants, perfumes, physiological coolants, antimicrobial agents and mixtures thereof. Other compositions of the invention take the form of bleach and/or detergent compositions which comprise the aminoalkylsilicone antiplaque agent and lipophile.

In general terms, the aminoalkylsilicone is selected from noncyclic, hydrophobic aminoalkysilicones having a formula comprising two basic units:
1) $(R^1)_m(R)_nSiO_{(4-m-n)/2}$ wherein m+n is 1, 2 or 3; n is 1, 2 or 3; m is 0,1,2; and
2) $(R^1)_a(R^2)_bSiO_{(4-a-b)/2}$ wherein a+b is 1, 2, or 3, and a and b are integers,
wherein $R^1$ and $R^2$ are independently selected from H, alkyl and alkenyl of about 1 to about 10 carbons optionally substituted with fluoro or cyano groups, hydroxy, alkoxy, and acetoxy, for example, wherein $R^1$ and $R^2$ are independently selected from methyl, ethyl, phenyl, vinyl, trifluoropropyl and cyanopropyl, and R is

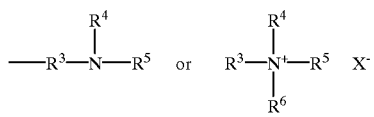

wherein $R^3$ is a divalent alkylene of about 1–20, preferably about 3–5 carbon atoms optionally substituted or interrupted by O atoms, $R^4$, $R^5$ and $R^6$ which may be the same or different are selected from H, alkyl of about 1–20, preferably about 1–10, more preferably about 1–4 carbons optionally substituted or interrupted by N and/or O atoms, and $X^-$ is a monovalent anion such as halide, hydroxide, and tosylate, said aminoalkylsilicone including from about 0.1–2%, preferably from about 0.5–2% of unit (1) on a repeating unit basis.

In a preferred embodiment, the aminoalkylsilicones comprise amodimethicones. Amodimethicones are polydimethylsiloxane polymers containing aminoalkyl groups. The aminoalkyl groups may be present either pendant or at one or more ends of the polydimethylsiloxane chain. Preferred are aminoalkylsilicones in which aminoalkyl moiety R is selected from $(CH_2)3NH_2$, $(CH_2)_3NHCH_2CH_2NH_2$, $(CH_2)_3N(CH_2CH_2OH)_2$, $(CH_2)_3NH_3^+X^-$, and $(CH_2)_3N(CH_3)_2(C_{18}H_{37})^+X^-$, and especially from $(CH_2)_3NH_2$ and $(CH_2)_3NHCH_2CH_2NH_2$. Also preferred are aminoalkyl silicones having an average molecular weight of about 5,000 and above, preferably from about 5000 to about 100,000, more preferably from about 5000 to about 30,000.

Aminoalkylsilicone compounds suitable for use herein are well known. Methods of preparing aminoalkylsilicones are given in, for example, U.S. Pat. No. 2,930,809.

Examples of amodimethicones include OSI's Magnasoft fluid. These polymers comprise aminoalkyl groups affixed to a predominantly polydimethylsiloxane structure. The typical structure of Magnasoft's aminoalkyl group-containing units is

—OSi(Me)C₃H₆NHCH₂CH₂NH₂.

The aminoalkylsilicone is generally present in a level of from about 0.01% to about 25%, preferably from about 0.1% to about 5%, more preferably from about 0.5% to about 1.5% by weight.

The compositions of the invention preferably also include a lipophilic compound. In general terms, lipophilic compounds suitable for use herein are oil-like materials which are soluble or solubilisable in the aminoalkylsilicone, preferably at a level of at least about 1%, more preferably at least about 5% by weight at 25° C. Preferred lipophilic compounds are selected from flavorants, perfumes, physiological cooling agents and antimicrobial compounds. The aminoalkylsilicone acts to enhance the substantivity of the lipophilic compound to a surface treated therewith, thereby providing enhanced and/or sustained flavor, perfume or coolant impact and/or antimicrobial efficacy.

Lipophilic flavorants suitable for use herein comprise one or more flavor components selected from wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

Lipophilic perfumes suitable for use herein comprise one or more known perfume components inclusive of natural products such as essential oils, absolutes, resins, etc., and synthetic perfume components such as hydrocarbons, alcohols, aldehydes, ketones, ethers, acids, esters, acetals, ketals, nitriles etc., including saturated and unsaturated compounds, aliphatic, carboxylic and heterocyclic compounds. Examples of perfume materials suitable for use herein include geranyl acetate, linalyl acetate, citronellyl acetate, dihydromyrcenyl acetate, terpinyl acetate, tricyclodecenyl acetate, tricyclodecenyl propionate, 2-phenylethyl acetate, benzyl acetate, benzyl salicylate, benzyl benzoate, styrallyl acetate, amyl salicylate, methyl dihydrojasmonate, phenoxyethyl isobutyrate, neryl acetate, trichloromethylphenylcarbinyl acetate, p-tertiary butyl-cyclohexyl acetate, isononyl acetate, cedryl acetate, vetiveryl acetate, benzyl alcohol, 2-phenylethanol, linalool, tetrahydrolinalool, citronellol, dimethylbenzylcarbinol, dihydromyrcenol, tetrahydromyrcenol, terpineol, eugenol, geraniol, vetiverol, 3-isocamphyl-cyclohexanol, 2-methyl-3-(p-tertiary butylphenyl)-propanol, 2-methyl-3-(p-isopropylphenyl)-propanol, 3-(p-tertiary butylphenyl)-propanol, nerol, alpha-n-amylcinnamic aldehyde, alpha-hexyl-cinnamic aldehyde, 4(4-hydroxy-4methylpentyl)-3-cyclohexenecarbaldehyde, 4-(4methyl-3-pentenyl)-3-cyclohexenecarbaldehyde, 4acetoxy-3-pentyl-tetrahydropyran, 2-n-heptyl-cyclopentanone, 3-methyl-2-pentyl-cyclopentanone, n-decanal, n-dodecanal, hydroxycitronellal, phenylacetaldehyde dimethyl acetal, phenylacetaldehyde diethyl acetal, geranonitrile, citronellonitrile, cedryl methyl ether, isolongifolanone, aubepine nitrile, aubepine, heliotropine, coumarin, vanillin, diphenyl oxide, ionones, methyl ionones, isomethyl ionones, irones, cis-3-hexenol and esters thereof, indane musks, tetralin musks, isochroman musks, macrocyclic ketones, macrolactone musks, ethylene brassylate, aromatic nitromusks and mixtures thereof.

Lipophilic antimicrobial compounds suitable for use herein include thymol, menthol, triclosan, 4-hexylresorcinol, phenol, eucalyptol, benzoic acid, benzoyl peroxide, butyl paraben, methyl paraben, propyl paraben, salicylamides, and mixtures thereof.

Physiological cooling agent suitable for use herein include carboxamides, menthane esters and menthane ethers, and mixtures thereof.

Suitable menthane ethers for use herein are selected from those with the formula:

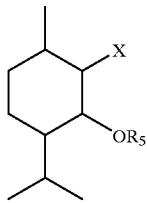

where $R_5$ is an optionally hydroxy substituted aliphatic radical containing up to 25 carbon atoms, preferably up to 5 carbon atoms, and where X is hydrogen or hydroxy, such as those commercially available under the trade name Takasago, from Takasago International Corporation. A particularly preferred cooling agent for use in the compositions of the present invention is Takasago 10 [3-1-menthoxy propan-1,2-diol (MPD)]. MPD is a monoglycerin derivative of 1-menthol and has excellent cooling activity.

The carboxamides found most useful are those described in U.S. Pat. No. 4,136,163, Jan. 23, 1979 to Wason et al., and U.S. Pat. No. 4,230,688, Oct. 28, 1980 to Rawsell et al.

The level of lipophilic compound in the compositions of the invention is generally in the range from about 0.01% to about 10%, preferably from about 0.05% to about 5%, more preferably from about 0.1% to about 3% by weight.

The compositions of the invention optionally include one or more surfactants, these being especially preferred in lipophilic compositions of the invention for the purpose of solubilization of the lipophile and for providing improved efficacy. Suitable surfactants include non-soap anionic, nonionic, cationic, zwitterionic and amphoteric organic synthetic detergents. Many of these suitable agents are disclosed by Gieske et al. in U.S. Pat. No. 4,051,234, Sep. 27, 1977.

Examples of surfactants suitable for use herein include $C_6$–$C_{18}$ alkyl sulfates and alkyl ether sulfates ethoxylated with from about 0.5 to about 20 moles of ethylene oxide per mole; anionic sulfonates inclusive of $C_5$–$C_{20}$ linear alkylbenzene sulfonates, alkyl ester sulfonates, $C_6$–$C_{22}$ primary or secondary alkane sulfonates, $C_6$–$C_{24}$ olefin sulfonates, sulfonated polycarboxylic acids, alkyl glycerol sulfonates, fatty acyl glycerol sulfonates, and mixtures thereof; anionic carboxylates inclusive of primary and secondary $C_6$ to $C_{18}$ alkyl carboxylate, ethoxy carboxylate and polyethoxy polycarboxylate surfactants having an average degree of ethoxylation of from about 0 to about 10; $C_5$–$C_{17}$ sarcosinates such as sodium cocoylsarcosinate, sodium lauroyl sarcosinate (Hamposyl-95 ex W. R. Grace); condensation products of ethylene or propylene oxide with fatty acids, fatty alcohols, fatty amides, polyhydric alcohols (e.g. sorbitan monostearate, sorbitan oleate), alkyl phenols (e.g. Tergitol) and polypropyleneoxide or polyoxybutylene (e.g. Pluronics); alkylpolysaccharides as disclosed in U.S. Pat. No. 4,565,647; amine oxides such as dimethyl cocamine oxide, dimethyl lauryl amine oxide and cocoalkyldimethyl amine oxide (Aromox); polysorbates such as Tween 40 and Tween 80 (Hercules); sorbitan stearates, sorbitan monooleate, etc; cationic surfactants such as cetyl pyridinium chloride, cetyl trimethyl ammonium bromide, di-isobutyl phenoxy ethoxy ethyl-dimethyl benzyl ammonium chloride and coconut alkyl trimethyl ammonium nitrate.

Highly preferred herein from the view point of lipophile solubilization are the nonionic surfactants. One class of nonionic surfactant suitable for use herein are those having the general formula:

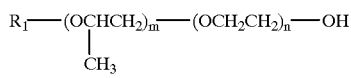

in which $R_1$ is an alk(en)yl or alk(en)yl phenyl group having 8 to 22, preferably 10 to 20 carbon atoms ion the alk(en)yl moiety and m and n represent weight-averages in the range 0–80 and 2–80 respectively. Shorter chain length alkyl groups are generally to be avoided for efficacy reasons and because unreacted fatty alcohol in such surfactants is a source of malodour and occasionally of skin irritation. It will be understood that surfactants of this type are usually mixtures of varying degrees of ethoxylation/propoxylation, accordingly m and n represent the respective weight-averages of the number of propoxylate and ethoxylate groups. Nonionic surfactants of the above general type include mixed alkoxylates in which m and n are both in the range from about 2 to about 80, with m preferably being in the range from about 2 to about 20, more preferably from about 3 to about 10 and with n preferably being in the range from about 2 to about 60, more preferably from about 5 to about 50. One such material is PPG-5-ceteth-20 (available from Croda Inc as Procetyl AWS), where m and n have the values 5 and 20 respectively. Other suitable nonionic surfactants include polyethoxylated surfactants, e.g. ethoxylated alkylphenol ethers, particularly octyl- and nonylphenol ethers containing 8–16 EO; ethoxylated aliphatic $C_8$–$C_{20}$ alcohols, which may be linear or branched and contain 8–16, preferably 9–15 EO; and ethoxylated hydrogenated castor oils.

In general, the ratio of surfactant to the perfume, coolant or other oily material will be in the range of from about 50:1 to about 1:10, preferably from about 20:1 to about 1:2, more preferably from about 10:1 to about 1:1.

Bleaching compositions of the invention additionally include one or more bleaching agents optionally together with organic peroxyacid precursors, effervescence generators, chelating agents, etc.

The bleaching agent takes the form of an inorganic persalt and can be selected from any of the well-known bleaching agents known for use in household bleaches, detergents, denture cleansers and the like such as the alkali metal and ammonium persulfates, perborates inclusive of mono-and tetrahydrates, percarbonates (optionally coated as described in GB-A-1,466,799) and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates, percarbonates and mixtures thereof are prefered for use herein, highly preferred being the alkali metal perborates and percarbonates.

The amount of bleaching agent in the bleaching compositions of the invention is generally from about 5 to about 70% preferably from about 10% to about 50%.

The bleaching compositions can also incorporate an effervescence generator which in preferred embodiments takes the form of a solid base material which in the presence of water releases carbon dioxide or oxygen with effervescence. The effervescence generator can be selected from generators which are effective under acid, neutral or alkaline pH conditions, but preferably it consists of a combination of a generator which is effective or most effective under acid or neutral pH conditions and a generator which is effective or most effective under alkaline pH conditions. Effervescence generators which are effective under acid or neutral pH conditions include a combination of at least one alkali metal carbonate or bicarbonate, such as sodium bicarbonate, sodium carbonate, sodium sesquicarbonate, potassium carbonate, potassium bicarbonate, or mixtures thereof, in admixture with at least one non-toxic, physiologically-acceptable organic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. Of these, malic acid is preferred. Effervescence generators which are effective under alkaline pH conditions include persalts such as alkali and alkaline earth metal peroxoborates as well as perborates, persulphates, percarbonates, perphosphates and mixtures thereof as previously described, for example, a mixture of an alkali metal perborate (anhydrous, mono- or tetrahydrate) with a monopersulphate such as Caroat$^R$ marketed by E I du Point de Nemours Co. and which is a 2:1:1 mixture of monopersulphate, potassium sulphate and potassium bisulphate and which has an active oxygen content of about 4.5%.

In preferred bleaching compositions suitable for use as denture cleansers, the solid base material incorporates a (bi)carbonate/acid effervescent couple optionally in combination with a perborate/persulphate oxygen effervescence generator. The combination of generators is valuable for achieving optimum dissolution characteristics and pH conditions for achieving optimum cleaning and antimicrobial activity. The (bi)carbonate components generally comprise from about 5% to about 65%, preferably from about 25% to 55% of the total composition; the acid components generally comprise from about 5% to about 50%, preferably from about 10% to about 30% of the total composition.

The bleaching compositions of the invention can be supplemented by other known components of such formulations. An especially preferred additional component is an organic peroxyacid precursor, which in general terms can be defined as a compound having a titre of at least 1.5 ml of 0.1N sodium thiosulfate in the following peracid formation test.

A test solution is prepared by dissolving the following materials in 1000 mls distilled water:

| | |
|---|---|
| sodium pyrophosphate ($Na_4P_2O_7 \cdot 10H_2O$) | 2.5 g |
| sodium perborate ($NaBO_2 \cdot H_2O_2 \cdot 3H_2O$) having 10.4% available oxygen | 0.615 g |
| sodium dodecylbenzene sulphonate | 0.5 g |

To this solution at 60° C. an amount of activator is added such that for each atom of available oxygen present one molecular equivalent of activator is introduced.

The mixture obtained by addition of the activator is vigorously stirred and maintained at 60° C. After 5 minutes from addition, a 100 ml portion of the solution is withdrawn and immediately pipetted onto a mixture of 250 g cracked ice and 15 ml glacial acetic acid. Potassium iodide (0.4 g) is then added and the liberated iodine is immediately titrated with 0.1 N sodium thiosulphate with starch as indicator until the first disappearance of the blue colour. The amount of sodium thiosulphate solution used in ml is the titre of the bleach activator.

The organic peracid precursors are typically compounds containing one or more acyl groups, which are susceptible to perhydrolysis. The preferred activators are those of the N-acyl or O-acyl compound type containing a acyl radical R—CO wherein R is a hydrocarbon or substituted hydrocarbon group having preferably from about 1 to about 20 carbon atoms. Examples of suitable peracid precursors include:

1) Acyl organoamides of the formula $RCONR_1R_2$, where RCO is carboxylic acyl radical, $R_1$ is an acyl radical and $R_2$ is an organic radical, as disclosed in U.S. Pat. No. 3,117,148. Examples of compounds falling under this group include:

a) N,N-diacetylaniline and N-acetylphthalimide;
   b) N-acylhydantoins, such as N,N'-diacetyl-5,5-dimethylhydantoin;
   c) Polyacylated alkylene diamines, such as N,N,N'N'-tetraacetylethylenediamine (TAED) and the corresponding hexamethylenediamine (TAHD) derivatives, as disclosed in GB-A-907,356, GB-A-907,357 and GB-A-907,358;
   d) Acylated glycolurils, such as tetraacetylglycoluril, as disclosed in GB-A-1,246,338, GB-A-1,246,339 and GB-A-1,247,429.

2) Acylated sulphonamides, such as N-methyl-N-benzoyl-menthane sulphonamide and N-phenyl-N-acetyl menthane sulphonamide, as disclosed in GB-A-3,183,266.

3) Carboxylic esters as disclosed in GB-A-836,988, GB-A-963,135 and GB-A-1,147,871. Examples of compounds of this type include phenyl acetate, sodium acetoxy benzene sulphonate, trichloroethylacetate, sorbitol hexaacetate, fructose pentaacetate, p-nitrobenzaldehyde diacetate, isopropeneyl acetate, acetyl aceto hydroxamic acid, and acetyl salicylic acid. Other examples are esters of a phenol or substituted phenol with an alpha-chlorinated lower aliphatic carboxylic acid, such as chloroacetylphenol and chloroacetylsalicylic acid, as disclosed in U.S. Pat. No. 3,130,165.

4) Carboxylic esters having the gernal formal Ac L wherein Ac is the acyl moiety of an organic carboxylic acid comprising an optionally substituted, linear or branched $C_6-C_{20}$ alkyl or alkenyl moiety or a $C_6-C_{20}$ alkyl-substituted aryl moiety and L is a leaving group, the conjugate acid of which has a pKa in the range from 4 to 13, for example oxybenzenesulfonate or oxybenzoate. Preferred compounds of this type are those wherein:

a) Ac is $R_3$—CO and $R_3$ is a linear or branched alkyl group containing from 6 to 20, preferably 6 to 12, more preferably 7 to 9 carbon atoms and wherein the longest linear alkyl chain extending from and including the carbonyl carbon contains from 5 to 18, preferably 5 to 10 carbon atoms, $R_3$ optionally being substituted (preferably alpha to the carbonyl moiety) by Cl, Br, OCH3 or $OC_2H_5$. Examples of this class of material include sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenzenesulfonate, the acyloxy group in each instance preferably being p-substituted;

b) Ac has the formula $R_3(AO)_mXA$ wherein $R_3$ is a linear or branched alkyl or alkylaryl group containing from 6 to 20, preferably from 6 to 15 carbon atoms in the alkyl moiety, $R_5$ being optionally substituted by Cl, Br, $OCH_3$, or $OC_2H_5$, AO is oxyethylene or oxypropylene, m is from 0 to 100, X is O, $NR_4$ or CO—$NR_4$, and A is CO, CO—CO, $R_6$—CO, CO—$R_6$—CO, or CO—NR$_4$—R$_6$—CO wherein R$_4$ is C$_1$–C$_4$ alkyl and R$_6$ is alkylene, alkenylene, arylene or alkarylene containing from 1 to 8 carbon atoms in the alkylene or alkenylene moiety. Bleach activator compounds of this type include carbonic acid derivatives of the formula R$_3$(AO)$_m$OCOL, succinic acid derivatives of the formula R$_3$OCO(CH$_2$)2COL, glycollic acid derivatives of the formula R$_{30}$CH$_2$COL, hydroxypropionic acid derivatives of the formula R$_3$OCH$_2$CH$_2$COL, oxalic acid derivatives of the formula R$_3$OCOCOL, maleic and fumaric acid derivatives of the formula R$_3$OCOCH=CHCOL, acyl aminocaproic acid derivatives of the formula R$_3$CONR$_1$(CH$_2$)$_6$COL, acyl glycine derivatives of the formula R$_3$CONR$_1$CH$_2$COL, and amino-6-oxocaproic acid derivatives of the formula R$_3$N(R$_1$)CO(CH$_2$)$_4$COL. In the above, m is preferably from 0 to 10, and R$_3$ is preferably C$_6$–C$_{12}$, more preferably C$_6$–C$_{10}$ alkyl when m is zero and C$_9$–C$_{15}$ when m is non-zero. The leaving group L is as defined above.

5) Acyl-cyanurates, such as triacetyl- or tribenzoylcyanurates, as disclosed in U.S. Pat. No. 3,332,882.

6) Optionally substituted anhydrides of benzoic or phthalic acid, for example, benzoic anhydride, m-chlorobenzoic anhydride and phthalic anhydride.

7) N-acylated precursor compounds of the lactam class as disclosed generally in GB-A-855735, especially caprolactams and valerolactams such as benzoyl valerolactam, benzoyl caprolactam and their substituted benzoyl analogs such as the chloro, amino, alkyl, aryl and alkoxy derivatives.

Of all the above, preferred are organic peracid precursors of types 1(c), 4(a) and 7.

Where present, the level of peroxyacid bleach precursor by weight of the total composition is preferably from about 0.1% to about 10%, more preferably from about 0.5% to about 5% and is generally added in the form of a bleach precursor agglomerate.

The bleach precursor agglomerates preferred for use herein generally comprise a binder or agglomerating agent in a level of from about 5% to about 40%, more especially from about 10% to about 30% by weight thereof. Suitable agglomerating agents include polyvinylpyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, phosphates and polyphosphates, clays, aluminosilicates and polymeric polycarboxylates. Of the above, polyethyleneglycols are highly preferred, especially those having molecular weight of from about 1,000 to about 30,000, preferably 2000 to about 10,000.

Preferred from the viewpoint of optimum dissolution and pH characteristics are bleach precursor agglomerates which comprise from about 10% to about 75%, preferably from about 20% to about 60% by weight thereof of peroxyacid bleach precursor, from about 5% to about 60% preferably from about 5% to about 50%, more preferably from about 10% to about 40% of a (bi) carbonate/acid effervescent couple, from about 0% to about 20% of a peroxoboroate, and from about 5% to about 40%, preferably from about 10% to about 30% of an agglomerating agent. The final bleach precursor granules desirably have an average particle size of from about 500 to about 1500, preferably from about 500 to about 1,000 um, this being valuable from the viewpoint of optimum dissolution performance and aesthetics. The level of bleach precursor agglomerates, moreover, is preferably from about 1% to about 20%, more preferably from about 5% to about 15% by weight of composition.

The bleaching compositions of the invention can be in paste, tablet, granular or powder form. Compositions in tablet form can be single or multiple layered tablets.

Bleaching compositions of the invention can be supplemented by other usual components of such formulations, especially surfactants as generally described above, chelating agents, enzymes, dyestuffs, sweeteners, tablet binders and fillers, foam depressants such as dimethylpolysiloxanes, foam stabilizers such as the fatty acid sugar esters, preservatives, lubricants such as talc, magnesium stearate, finely divided amorphous pyrogenic silicas, etc.

Tablet binders and fillers suitable for use herein include polyvinylpyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, clays, polymeric polycarboxylates, sodium carbonate, calcium carbonate, calcium hydroxide, magnesium oxide, magnesium hydroxide carbonate, sodium sulfate, proteins, cellulose ethers, cellulose esters, polyvinyl alcohol, alginic acid esters, vegetable fatty materials of a pseudocolloidal character. Of the above, polyethyleneglycols are highly preferred, especially those having molecular weight of from about 1,000 to about 30,000, preferably from about 12,000 to about 30,000.

Chelating agents beneficially aid cleaning and bleach stability by keeping metal ions, such as calcium, magnesium, and heavy metal cations in solution. Examples of suitable chelating agents include sodium tripolyphosphate, sodium acid pyrophosphate, tetrasodium pyrophosphate, aminopolycarboxylates such as nitrilotriacetic acid and ethylenediamine tetracetic acid and salts thereof, ethylenediamine-N,N'-disuccinic acid (EDDS) and salts thereof, and polyphosphonates and aminopolyphosphonates such as hydroxyethanediphosphonic acid, ethylenediamine tetramethylenephosphonic acid, diethylenetriaminepentamethylenephosphonic acid and salts thereof. The chelating agent selected is not critical except that it must be compatible with the other ingredients of the denture cleanser when in the dry state and in aqueous solution. Advantageously, the chelating agent comprises between 0.1 and 60 percent by weight of the composition and preferably between 0.5 and 30 percent. Phosphonic acid chelating agents, however, preferably comprise from about 0.1 to about 1 percent, preferably from about 0.1% to about 0.5% by weight of composition.

Enzymes suitable for use herein are exemplified by proteases, alkalases, amylases, fungal and bacterial lipases, dextranases, mutanases, glucanases, esterases, cellulases, pectinases, lactases and peroxidases, etc. Suitable enzymes are discussed in U.S. Pat. No. 3,519,570 and U.S. Pat. No. 3,533,139.

The following Examples further describe and demonstrate the preferred embodiments within the scope of the present invention.

EXAMPLES I TO V

The following are representative denture cleansing tablets according to the invention. The percentages are by weight of the total tablet. The tablets are made by compressing a mixture of the granulated components in a punch and dye tabletting press at a pressure of about 105 kPa.

|                              | I    | II   | III  | IV   | V    |
|------------------------------|------|------|------|------|------|
| Malic Acid                   | 12   | 10   | 15   | —    | 14   |
| Citric Acid                  | —    | 10   | —    | 15   | —    |
| Sodium Carbonate             | 10   | 8    | 10   | 6    | 10   |
| Sulphamic Acid               | 5    | —    | —    | 3    | 3    |
| PEG 20,000                   | —    | 3    | 7    | 8    | 5    |
| PVP 40,000                   | 6    | 3    | —    | —    | —    |
| Sodium Bicarbonate           | 23   | 24   | 25   | 23   | 24   |
| Sodium Perborate Monohydrate | 15   | 12   | 16   | 30   | 15   |
| Potassium Monopersulphate    | 15   | 18   | 13   | —    | 14   |
| Pyrogenic Silica             | —    | 3    | 1    | 1    | —    |
| Talc                         | 2    | —    | —    | —    | —    |
| EDTA                         | —    | —    | 1    | —    | 3    |
| EDTMP[1]                     | 1    | —    | —    | 1    | —    |
| Flavor[5]                    | 2    | 1    | 2    | 1    | 2    |
| Magnasoft Fluid[4]           | 1    | 1.5  | 0.5  | 2    | 1    |
| Bleach Precursor Agglomerate | 9    | 8    | 10   | 12   | 10   |
| Bleach Precursor Agglomerate |      |      |      |      |      |
| TAED[2]                      | 2    | —    | 4    | 5    | 2.5  |
| TMHOS[3]                     | 2    | 3    | —    | —    | —    |
| Sulphamic Acid               | 2    | 2    | 2    | 2    | 3.5  |
| Sodium Bicarbonate           | 0.5  | 0.2  | 0.2  | 0.5  | 2    |
| PEG 6000                     | 2.5  | 2    | 2.4  | 2.5  | 1.5  |
| Dye                          | —    | 0.8  | 1.4  | 2    | 0.5  |

[1] Ethylenediaminetetramethylenephosphonic acid
[2] Tetraacetylethylene diamine
[3] Sodium 3,5,5-trimethylhexanoyloxybenzene sulfonate
[4] Magnasoft Fluid - supplied by OSI
[5] Peppermint-based flavor In Examples I to V above, the overall tablet weight is 3 g; diameter 25 mm.

The denture cleansing tablets of Examples I to V display improved antiplaque, cleansing and anti-bacterial activity together with excellent cohesion and other physical and in-use performance characteristics.

EXAMPLES VI TO IX

The following are representative perfume, flavour, coolant and antimicrobial compositions according to the invention. The percentages are by weight of total composition.

|                             | VI   | VII  | VIII | IX   |
|-----------------------------|------|------|------|------|
| PPG-5-ceteth-20             | 3.0  | 3.0  | 4.5  | 3.0  |
| PEG-40 hydrogenated castor oil | —  | 1.8  | 4.5  | 3.0  |
| Trideceth-12                | 2.0  | —    | —    | —    |
| Trideceth-9                 | —    | 2.0  | —    | 3.0  |
| Flavor[5]                   | 2.0  | —    | 3.0  | —    |
| Perfume[6]                  | —    | 3.0  | —    | —    |
| Trimethyl butanamide        | 0.3  | 0.5  | —    | —    |
| Triclosan                   | —    | —    | 1.0  | 0.5  |
| Magnasoft Fluid[4]          | 1.0  | 1.5  | 5.0  | 1.0  |
| Water                       | <---- ---- to 100% ---- ---- > | | | |

The perfume, flavor, coolant and/or antimicrobial compositions of Examples VI to IX display improved surface-substantivity, impact and/or efficacy.

I claim:

1. A method of improving the stability of a bleach and lipophile composition comprising an inorganic persalt bleaching agent and a lipophile selected from the group consisting of flavorants, perfumes, physiological coolants, antimicrobial agents and mixtures thereof, by inclusion of a aminoalkyl silicone having an aminoalkyl siloxane content of from 0.1% to 2% on a repeating unit basis.

2. The method of claim 1 wherein the composition is a denture cleanser.

3. The method of claim 1 wherein the inorganic persalt bleaching agent comprises one or more bleaching agents selected from the group consisting of alkali metal persulfates, alkali metal perborates and mixtures thereof.

4. The method of claim 1 wherein the flavorant comprises one or more flavor components selected from the group consisting of wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

5. The method of claim 1 wherein the perfume comprises one or more perfume components selected from the group consisting geranyl acetate, linalyl acetate, citronellyl acetate, dihydromyrcenyl acetate, terpinyl acetate, tricyclodecenyl acetate, tricyclodecenyl propionate, 2-phenylethyl acetate, benzyl acetate, benzyl salicylate, benzyl benzoate, styrallyl acetate, amyl salicylate, methyl dihydrojasmonate, phenoxyethyl isobutyrate, neryl acetate, trichloromethylphenylcarbinyl acetate, p-tertiary butyl-cyclohexyl acetate, isononyl acetate, cedryl acetate, vetiveryl acetate, benzyl alcohol, 2-phenylethanol, linalool, tetrahydrolinalool, citronellol, dimethylbenzylcarbinol, dihydromyrcenol, tetrahydromyrcenol, terpineol, eugenol, geraniol, vetiverol, 3-isocamphyl-cyclohexanol, 2-methyl-3-(p-tertiary butylphenyl)-propanol, 2-methyl-3-(p-isopropylphenyl)-propanol, 3-(p-tertiary butylphenyl)-propanol, nerol, alpha-n-amylcinnamic aldehyde, alpha-hexyl-cinnamic aldehyde, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 2-n-heptyl-cyclopentanone, 3-methyl-2-pentyl-cyclopentanone, n-decanal, n-dodecanal, hydroxycitronellal, phenylacetaldehyde dimethyl acetal, phenylacetaldehyde diethyl acetal, geranonitrile, citronellonitrile, cedryl methyl ether, isolongifolanone, aubepine nitrile, aubepine, heliotropine, coumarin, vanillin, diphenyl oxide, ionones, methyl ionones, isomethyl ionones, irones, cis-3-hexenol and esters thereof, indane musks, tetralin musks, isochroman musks, macrocyclic ketones, macrolactone musks, ethylene brassylate, aromatic nitromusks/8nd mixtures thereof.

6. The method of claim 1 additionally comprising an effervescence generator.

7. The method of claim 1 wherein the aminoalkylsilicone is a noncyclic, hydrophobic aminoalkylsilicone having a formula comprising two basic units:

1) $(R^1)_m(R)_n SiO_{(4-m-n)/2}$ wherein m+n is 1, 2 or 3; n is 1, 2 or 3; m is 0, 1, 2; and 2) $(R^1)_a(R^2)_b SiO_{(4-a-b)/2}$ wherein a+b is 1, 2, or 3, and a and b are integers, wherein $R^1$ and $R^2$ are independently selected from the group consisting of H, alkyl and alkenyl of about 1 to about 10 carbons optionally substituted with fluoro or cyano groups, hydroxy, alkoxy, and acetoxy, and R is

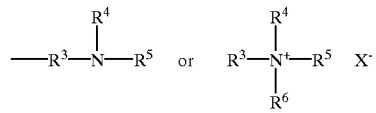

wherein $R^3$ is a divalent alkylene of about 1–20 carbon atoms optionally substituted or interrupted by O atoms, $R^4$, $R^5$ and $R^6$ which may be the same or different are selected from the group consisting H, alkyl of about 1–20 carbons optionally substituted or interrupted by N, O atoms and mixtures thereof, and $X^-$ is a monovalent anion.

8. The method of claim 7 wherein the aminoalkyl silicone has a molecular weight of at least about 5,000.

9. The method of claim 8 wherein the aminoalkyl silicone has a molecular weight of from about 5000 to about 100,000.

10. The method of claim 1 comprising from about 0.01% to about 25%, by weight of the aminoalkyl silicone.

11. The method of claim 10 comprising from about 0.1% to about 5% by weight of the aminoalkyl silicone.

12. The method of claim 1 additionally comprising an organic peroxyacid bleach precursor.

13. The method of claim 12 wherein the organic peroxyacid bleach precursor is selected from the group consisting of acylated polyalkyldiamines, especially tetraacetylethylenediamine, and carboxylic esters having the general formula AcL wherein Ac is the acyl moiety or an organic carboxylic acid comprising an optionally substituted, linear or branched $C_6$–$C_{20}$ alkyl or alkenyl moiety or a $C_6$–$C_{20}$ alkyl-substituted aryl moiety and L is a leaving group, the conjugate acid of which has a pKa in the range from 4 to 13.

* * * * *